United States Patent [19]

Podszun et al.

[11] Patent Number: 5,763,622
[45] Date of Patent: Jun. 9, 1998

[54] URETHANE (METH) ACRYLATES CONTAINING CYCLIC CARBONATE GROUPS

[75] Inventors: Wolfgang Podszun, Köln; Joachim Krüger, Monheim; Werner Finger, Neuss; Ludger Heiliger, Leverkusen; Carl Casser, Köln, all of Germany

[73] Assignee: Bayer AG, Leverkusen, Germany

[21] Appl. No.: 754,234

[22] Filed: Nov. 20, 1996

[30] Foreign Application Priority Data

Nov. 30, 1995 [DE] Germany ............ 195 44 671.2

[51] Int. Cl.$^6$ ............ C07D 317/34; A61K 6/08
[52] U.S. Cl. ............ 549/229; 514/467; 430/302; 523/115; 523/116; 433/228.1
[58] Field of Search ............ 549/230, 229; 514/467; 523/115, 116

[56] References Cited

U.S. PATENT DOCUMENTS

| | | | |
|---|---|---|---|
| 4,400,159 | 8/1983 | Orlowski et al. | 433/202 |
| 4,758,615 | 7/1988 | Engel et al. | 549/230 X |
| 4,904,750 | 2/1990 | Reiners et al. | 526/301 |
| 4,952,241 | 8/1990 | Reiners et al. | 106/35 |
| 5,621,119 | 4/1997 | Podszun et al. | 549/229 |

FOREIGN PATENT DOCUMENTS

| | | |
|---|---|---|
| 0 264 551 | 4/1988 | European Pat. Off. . |
| 0 321 841 | 6/1989 | European Pat. Off. . |
| 0 489 203 | 6/1992 | European Pat. Off. . |
| 0 579 503 | 1/1994 | European Pat. Off. . |
| 0 667 560 | 8/1995 | European Pat. Off. . |
| 0 693 487 | 1/1996 | European Pat. Off. . |
| 195 30 225 | 6/1996 | Germany . |
| WO 95/03294 | 2/1995 | WIPO . |

OTHER PUBLICATIONS

Orbit Abstract of DE 195 30 225 (Jun. 13, 1996).
Orbit Abstract of WO 97/07170 (Feb. 27, 1997).
Orbit Abstract of EP 0 264 551 (Apr. 27, 1988).
Orbit Abstract of EP 0 321 841 (Jun. 28, 1989).
Orbit Abstract of WO 95/03294 (Feb. 02, 1995).
Orbit Abstract of EP 0 667 560 (Aug. 16, 1995).
English language version of WO 95/03294 disclosure (Feb. 02, 1995).
English language version of EP 0 667 560 disclosure (Aug. 16, 1995).
English language version of EP 0 693 487 disclosure (Jan. 24, 1996).

*Primary Examiner*—Fiona T. Powers
*Attorney, Agent, or Firm*—Connolly & Hutz

[57] ABSTRACT

The invention relates to urethane acrylates and urethane methacrylates containing cyclic carbonate groups, and use thereof in dental materials and lithographic plates.

4 Claims, No Drawings

URETHANE (METH) ACRYLATES CONTAINING CYCLIC CARBONATE GROUPS

The invention relates to urethane acrylates and urethane methacrylates containing cyclic carbonate groups, and the use thereof in dental materials.

Urethane (meth)acrylates are widely used, for example, for coatings, in adhesives and in the field of dentistry. A monomer used particularly frequently in the field of dentistry is the conversion product of 2,2,4-trimethylhexamethylene diisocyanate and 2-hydroxy-ethyl methacrylate corresponding to formula (I).

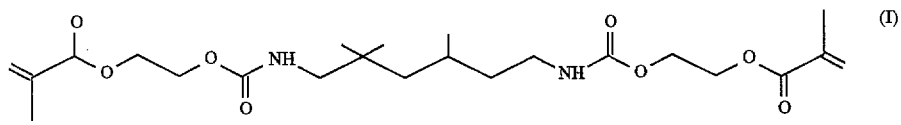

Compound (I) is used, for example, as a constituent of plastic filling materials, dental coatings, sealants, fixing materials and lining materials.

In U.S. Pat. No. 4,400,159 adducts of 3-methacryloyl-2-hydroxypropyl esters and diisocyanates are proposed as monomers for dental materials. This class of monomers corresponds to the general formula (II),

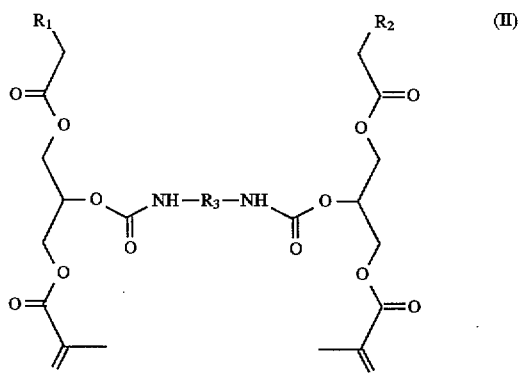

wherein $R_1$ and $R_2$ can signify, for example, a cyclohexyl group or phenyl group and $R_3$ an aliphatic, cycloaliphatic or aromatic radical having 6 to 14 carbon atoms.

Materials consisting of urethane (meth)acrylates have a favourable level of mechanical properties. Photopolymerisation under irradiation by visible light is a preferred method of curing for many applications. The duration of exposure necessary for curing dental filling materials is usually 15 to 60 s. The depths of curing are generally several mm and are definitely lower in highly pigmented filling materials than they are in transparent filling materials. If the cavities are deep, the dentist has to cure the filling in layers.

A shortcoming in all hitherto known photopolymerisable dental materials is that when in contact with atmospheric oxygen they do not cure at the free surface. This phenomenon, which is known as polymerisation inhibition, necessitates special measures to exclude atmospheric oxygen. A very effective measure in the case of smooth surfaces is that of covering with a transparent film which is impermeable to oxygen. For geometrically complicated surfaces, protective films (for example, of polyvinyl alcohol) applied from solution have been suggested as oxygen barriers, but this method is not only expensive but is also not very effective. In many cases the dentist resorts to the method of using an excess of dental material and removing the unpolymerised part in a finishing step after the exposure. This method also has serious disadvantages: the surface geometry can be created only very inaccurately. The boundary between unpolymerised or insufficiently polymerised material on the one side and completely cured material on the other is not discernible, so that there is the danger that in the finishing step a surface is obtained which is not optimally cured.

The object of the present invention is the provision of novel monomers having an increased polymerisation rate and lowered sensitivity to polymerisation inhibition owing to oxygen, in particular for applications in the field of dentistry.

The object of the invention is fulfilled by monomers containing cyclic carbonate groups corresponding to formula III

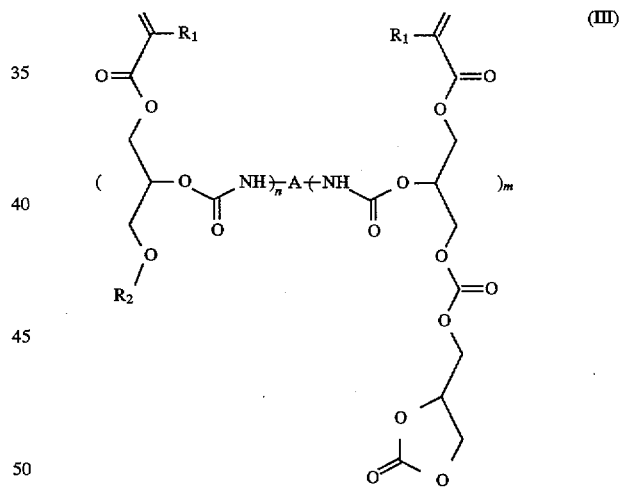

wherein $R_1$ represents hydrogen or methyl, $R_2$ represents hydrogen or (meth)acryl, A represents an n- and m-valent hydrocarbon radical having 2 to 30 carbon atoms, which can be interrupted by one or more ether, ester, amide, urethane or urea groups and can be substituted by one to five (meth) acrylate groups, n signifies an integer from 0 to 3 and m signifies an integer from 1 to 4.

Monomers corresponding to formula IIIa are preferred

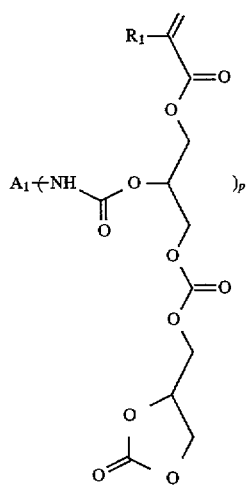 (IIIa)

wherein

R$_1$ represents hydrogen or methyl,

A$_1$ represents a p-valent hydrocarbon radical having 2 to 30 carbon atoms, which can be interrupted by one or more other, ester, amide, urethane or urea groups, p signifies 2 or 3

The monomers according to the invention can exist in different stereoisomeric structures, with only a part of the possible structures being recorded exactly by formula (III). By way of example, a stereoisomer is represented in formula (IIIb). The monomers according to the invention relate to all possible stereoisomers and combinations thereof.

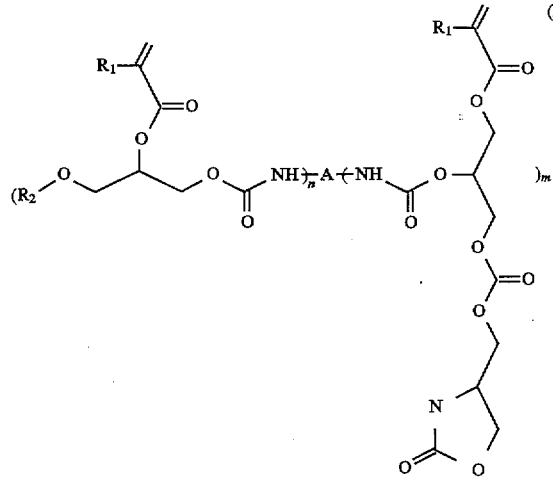 (IIIb)

The following may be mentioned as suitable hydrocarbon radicals A or A$_1$:

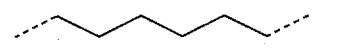
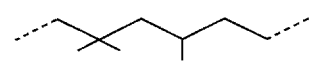
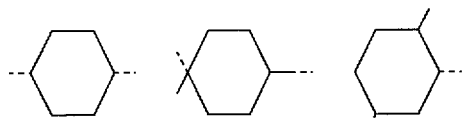
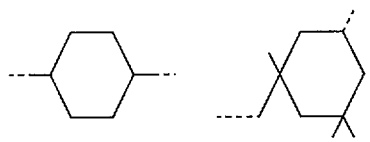
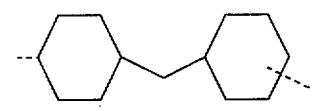
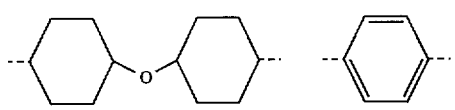
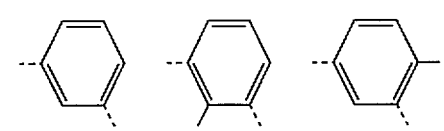
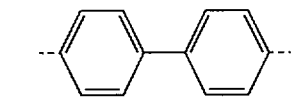
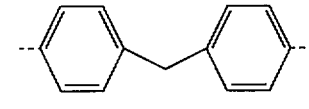
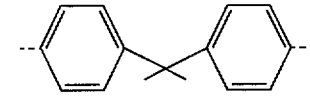

TABLE 1
Monomers according to the invention
Monomer 1
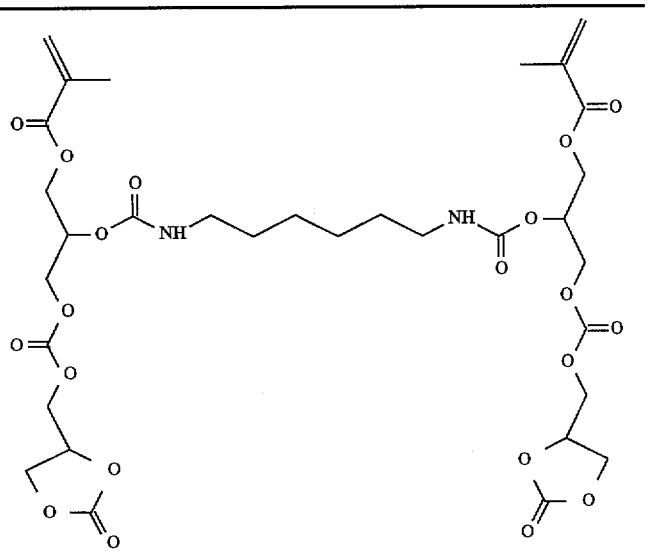
Monomer 2
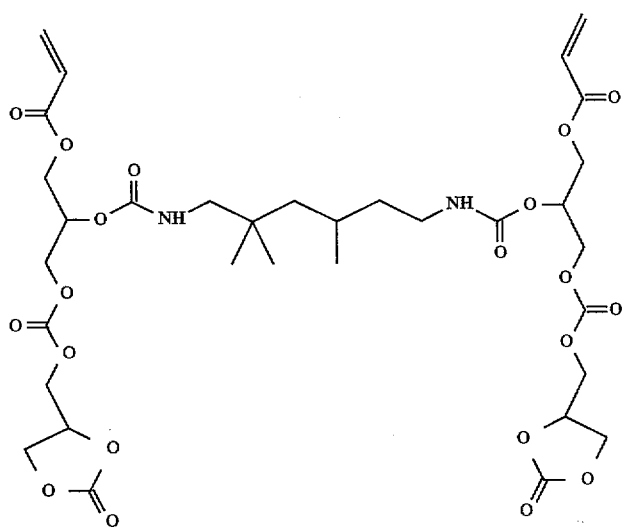
Monomer 3
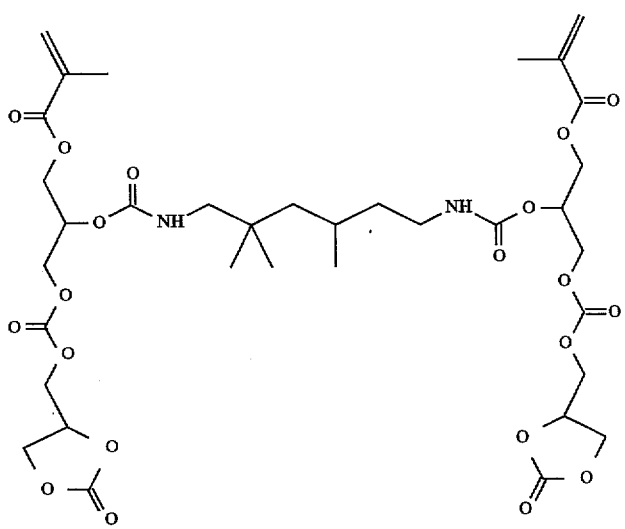

TABLE 1-continued
Monomers according to the invention
Monomer 4
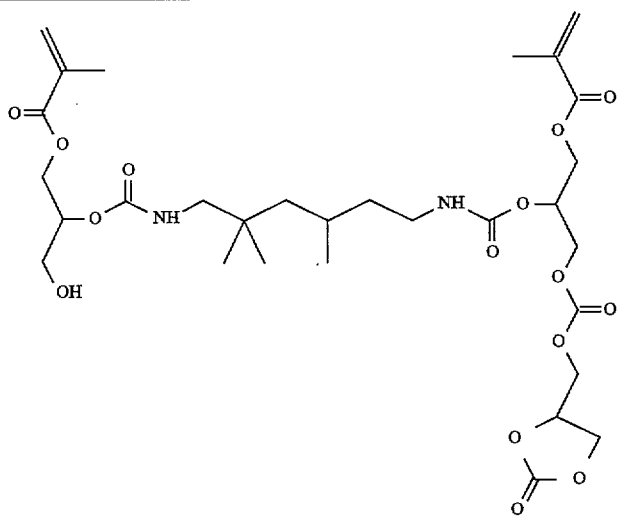
Monomer 5
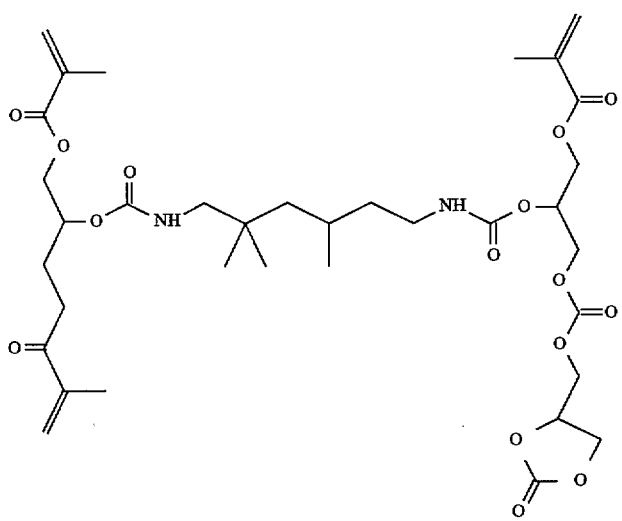
Monomer 6
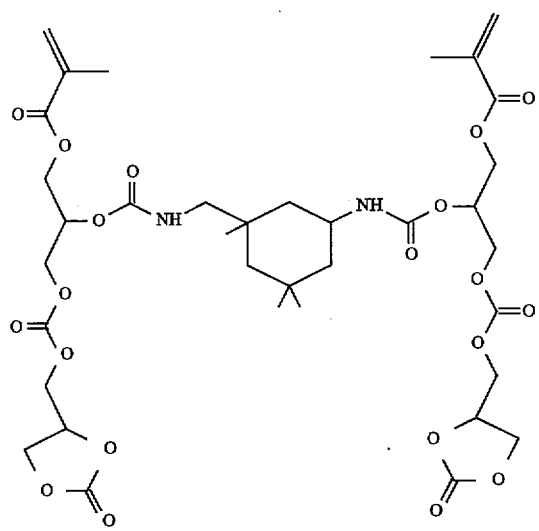

TABLE 1-continued
Monomers according to the invention
Monomer 7
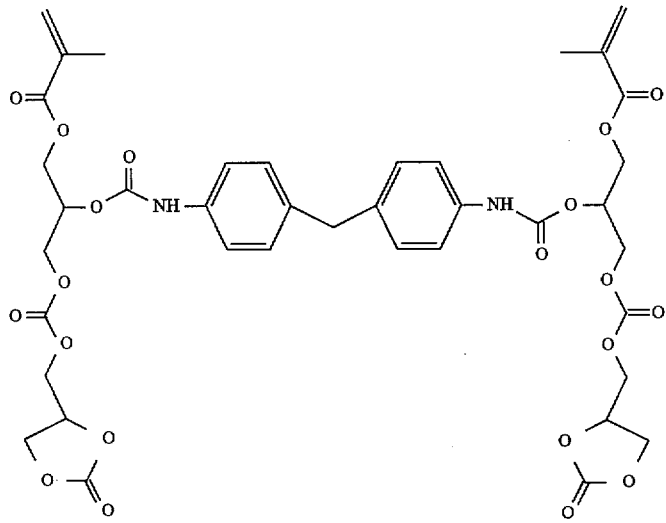
Monomer 8
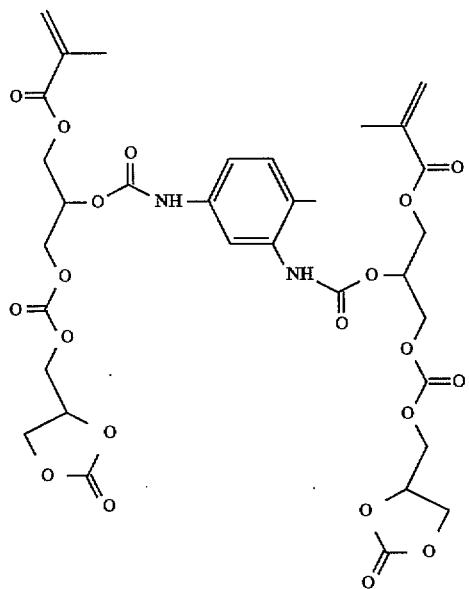

TABLE 1-continued
Monomers according to the invention
Monomer 9
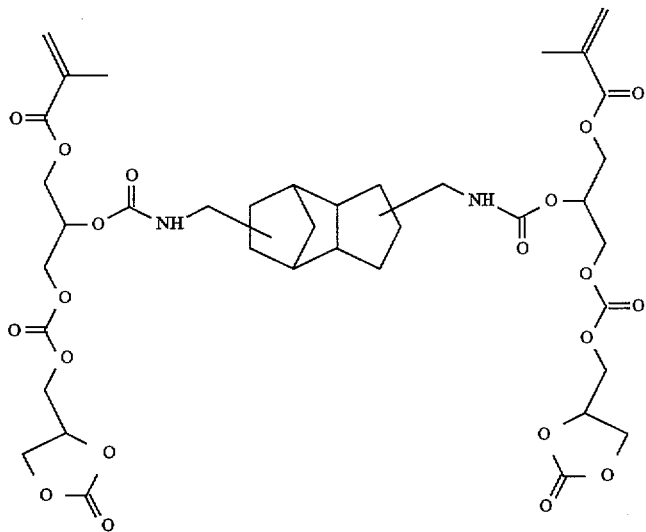
Monomer 10
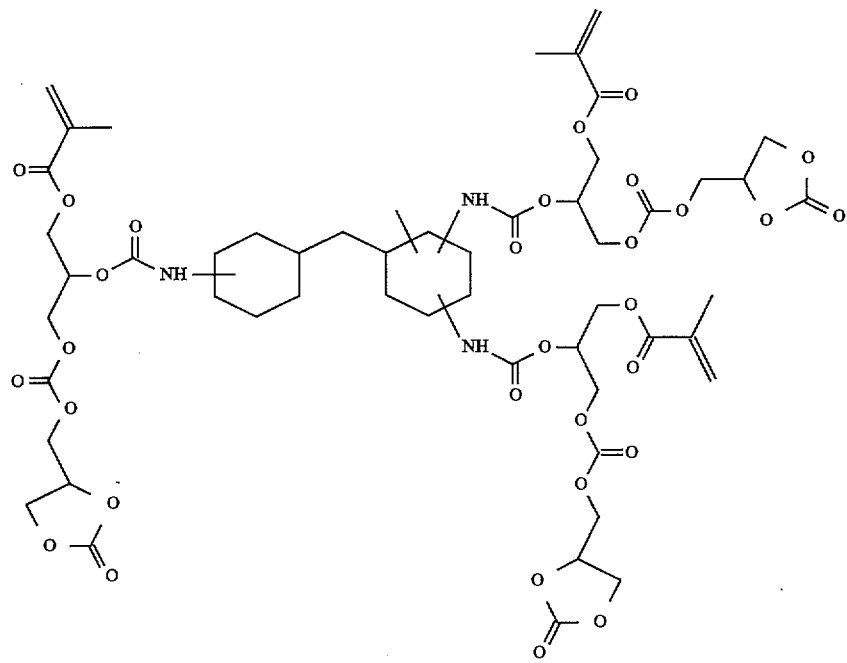

TABLE 1-continued

Monomers according to the invention

Monomer 11

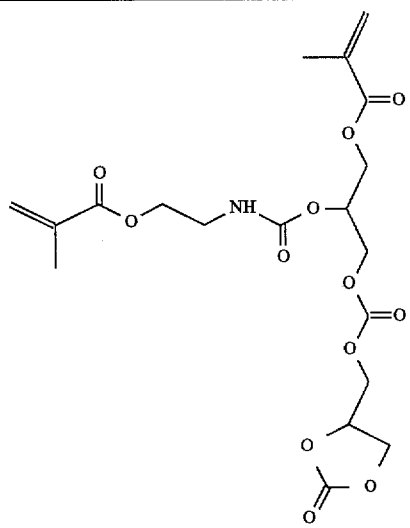

The synthesis of the urethane (meth)acrylates according to the invention containing cyclic carbonate groups is suitably carried out by the stoichiometric reaction of the hydroxyl compound corresponding to formula IV, optionally mixed with other hydroxyfunctional (meth)acrylate esters, with a mono-, di-, tri- or tetraisocyanate.

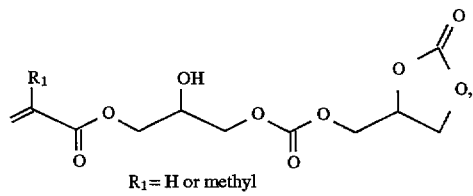

$R_1$ = H or methyl       (IV)

The said reaction is carried out preferably in an inert solvent in the presence of a catalyst at temperatures of, for example, −20° C. to 60° C. Examples of inert solvents which may be mentioned are acetone, butanone-2, tetrahydrofuran, methylene chloride, chloroform, toluene and acetonitrile. The catalyst used can be metal salt of higher fatty acids such as, for example, dibutyltin dilaurate, triaryl compounds such as, for example, triphenylstibine or triphenylphosphine, or tertiary amines such as, for example, triethylamine.

The hydroxyl compound corresponding to formula IV is obtainable, for example, by the reaction of glycerol mono (meth)acrylate with the chloroformate corresponding to formula V. The chloroformate corresponding to formula V can be prepared by phosgenation of glycerol. This preparative step is described in detail in U.S. Pat. No. 2,446,145.

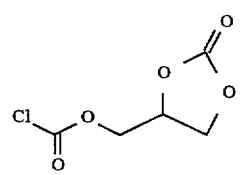        (V)

The hydroxyl compound IV can also be synthesised by the reaction of glycidol with the acid chloride (V) and subsequent opening of the epoxy ring by (meth)acrylic acid.

Compound IV is obtainable in particularly high purity by means of this procedural variant.

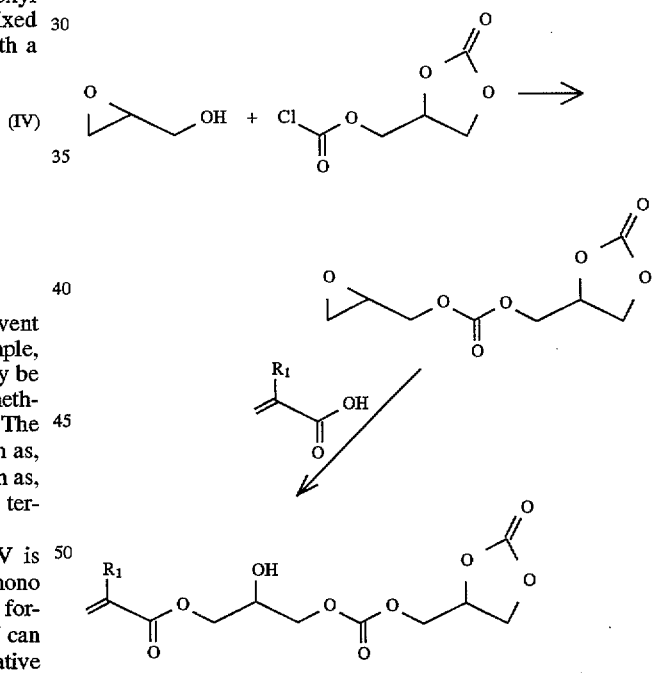

For the application of the monomers according to the invention in polymerisable dental restoration materials, the urethane (meth)acrylates according to the invention can be mixed with known per se monomers. Suitable components of the mixture are, for example, the so-called BisGMA and urethane methacrylates, for example, the compound corresponding to formula I.

The viscosity of the monomers according to the invention is suitable for many applications. If an even lower viscosity is desired, comonomers of lower viscosity can be added as reactive diluents or solvents to the monomers according to the invention. The compounds according to the invention are used in the mixture with the comonomers in a quantity of about 10 to 100 wt. %, preferably of from 20 to 80 wt. %.

The following comonomers may be mentioned as examples: glycerol dimethacrylate, triethylene glycol dimethacrylate, (TEGDMA), tetraethylene glycol dimethacrylate, 1,12-dodecanediol dimethacrylate, 1,6-hexanediol dimethacrylate, diethylene glycol dimethacrylate, 2,2-bis-[p-(2'-hydroxy-3'-methaeryloyloxypropoxy)-phenyl]-propane, 2,2-bis[p-(2'-methacryloyloxyethoxy)-phenyl]propane, trimethylolpropane tri(meth)acrylate, bis(meth)acryloyloxyethoxymethyl-tricyclo-[5.5.1.0$^{2.6}$]-decane (DE-A 2 931 925 and DE-A 2 931 926).

Comonomers which at 13 mbar have a boiling point of above 100° C. are particularly preferred.

The (meth)acrylates according to the invention can be cured to form cross-linked polymers by known per se methods, optionally in mixtures with the above-mentioned comonomers (Am. Chem. Soc. Symp. Ser.212, 359–371 (1983)). A system comprising a peroxide compound and a reducing agent, for example, based on a tertiary aromatic amine, is suitable for the so-called redox polymerisation. Examples of peroxides are dibenzoyl peroxide, dilauroyl peroxide and di-4-chlorobenzoyl peroxide.

Examples of tertiary aromatic amines which may be mentioned are N,N-dimethyl-p-toluidine, bis(2-hydroxyethyl)-p-toluidine, bis(2-hydroxy-ethyl)-3,5-dimethylaniline and N-methyl-N-(2-methylcarbamoyloxypropyl)-3,5-dimethylaniline. The concentration of the peroxide and of the amine respectively are advantageously chosen so as to be from 0.1 to 5 wt. %, preferably from 0.5 to 3 wt. %, referred to the mixture of monomers.

The peroxide-containing and amine-containing mixtures of monomers are stored separately until use.

The monomers according to the invention can be caused to polymerise by irradiation with UV light or visible light (for example, within the wavelength range of 230 to 650 nm). Suitable initiators for the photoinitiated polymerisation are, for example, benzil, benzil dimethyl ketal, benzoin monoalkyl ether, benzophenone, p-methoxy-benzophenone, fluorenone, thioxanthone, phenanthrenequinone and 2,3-bornanedione (camphorquinone), optionally in the presence of synergistically acting activators, such as N,N-dimethylaminoethyl methacrylate, triethanolamine, 4-N,N-dimethylaminobenzenesulphonyl-diallylamide. The carrying out of the photopolymerisation is described, for example, in DE-PS 3,135,115.

In addition to the above-mentioned initiators, light protection agents and stabilisers known per se for this purpose can be added to the monomers according to the invention.

Light protection agents are described, for example, in "G ächter, Müller, Taschen-buch der Kunststoff-Additive, 2nd Edition, Carl Hanser Verlag". The following light protection agents may be mentioned as examples: Cyasorb UV 9®, Tinuvin P®, Tinuvin 770®, Tinuvin 622®, Tinuvin 765®.

Stabilisers are described, for example, in "Ullmanns Encyclopädie der technischen Chemie, 4th Edition, Volume 8". The following stabilisers may be mentioned as examples:

2,6-di-tert.-butylphenol, 2,6-di-tert.-butyl-4-methylphenol, 2,6-dioctadecyl-4-methylphenol, 1,1'-methylenebis (naphthol-2) et cetera.

The light protection agents and the stabilisers may each be used in a quantity of from 0.01 to 0.5 parts by weight, referred to 100 parts by weight of the mixture of monomers.

The mixtures of monomers, with or without the addition of fillers, may also be used as coating materials (dental coatings) and as adhesives (enamel and dentine).

Fillers are generally added to the mixtures of monomers obtained when they are used as dental filling materials and fixing materials. Mixtures of monomers having a viscosity in the range of 60 to 10,000 mPa.s are particularly advantageous for achieving a high degree of filling.

It is preferable to add inorganic fillers to the monomers according to the invention. Examples which may be mentioned are rock crystal, cristobalite, quartz glass, highly disperse silica, aluminium oxide and glass ceramics, for example, glass ceramics containing zirconium (DE-OS 2,347,591). The inorganic fillers are preferably previously treated with a bonding agent in order to improve the bonding of the polymethacrylate to the polymer matrix. The bonding can be achieved, for example, by a treatment with organo-silicon compounds (Progress in Organic Coatings 11, 297–308 (1983)). Preferably 3-methacryloyloxy-propyltrimethoxysilane is used. The fillers for the dental filling materials according to the invention generally have an average particle diameter of from 0.01 to 100 μm, preferably of from 0.03 to 50 μm, particularly preferably of from 0.03 to 5 μm. The simultaneous use of several fillers having a differing average particle diameter and/or a different silane content may also be advantageous.

The proportion of filler, both in the dental filling material and in the fixing material, is generally 5 to 85 wt. %, preferably 50 to 80 wt. %.

To prepare the restoration materials, the components are mixed together using commercial kneaders.

The proportion of the (meth)acrylates according to the invention in the restoration materials is generally from 5 to 60 wt. %, referred to the restoration material.

Dental coatings, adhesives and restoration materials which contain the monomers according to the invention exhibit an extremely high polymerisation rate, with the polymerisation being only a little inhibited by atmospheric oxygen. Large curing depths are achieved during photopolymerisation.

To examine the sensitivity of the monomers according to the invention to polymerisation inhibition owing to atmospheric oxygen, the unpolymerised layer thickness was determined by measuring the sample surface prior to and after dissolution of the monomer layer in a suitable solvent.

The monomers according to the invention can furthermore be used for the production of lithographic plates.

EXAMPLES

Example 1

Preparation of monomer 1 in Table 1

32.0 g of glycerol monomethacrylate, 32.38 g of triethylamine, 0.08 g of 2,6-di-tert.-butyl cresol (stabiliser) and 0.08 g of dibutyltin dilaurate (catalyst) were dissolved in 300 g of chloroform under an atmosphere of nitrogen and cooled to −10° C. 54.17 g of chloroformate of formula V, dissolved in 100 g of chloroform, was then added over a period of 30 min and the batch was stirred for a further 20 h at room temperature. 16.8 g of hexamethylene diisocyanate was then added dropwise over a period of 30 min. Stirring was continued (about 10 h) until no NCO band was detectable in the IR spectrum. The precipitate formed was filtered off and the filtrate was poured onto twice its volume of water. The organic phase was separated off, washed 4 times with water and dried over sodium sulphate. After the solvent had been filtered and evaporated off, there remained 64.6 g of monomer 1 in Table 1.

IR [cm$^{-1}$]: 1,800 (cyclic carbonate); 1,720 (urethane); 1,640 (methacryl).

Example 2

Preparation of the monomers 3, 6, 8, 9, 10 and 11 in Table 1

The experiments were carried out as described in Example 1, except that instead of 16.8, g of hexamethylene diisocyanate the monomers listed below were used in the stated quantities.

| Monomer in Table 1 | Isocyanate | Quantity used |
|---|---|---|
| Monomer 3 | 2,2,4-trimethylhexamethylene diisocyanate | 21.0 g |
| Monomer 6 | Isophorone diisocyanate | 22.2 g |
| Monomer 8 | 1,3-tolylene diisocyanate | 17.4 g |
| Monomer 9 | Bisisocyanatomethyltricyclo-(5,2,1)-decane | 24.6 g |
| Monomer 10 | Triisocyanatomethyl dicyclohexyl-methane (isomeric mixtures having an NCO content of 37 wt. %) | 21.2 g |
| Monomer 11 | 2-isocyanatoethyl methacrylate | 31.0 g |

Example 3
Examination of the photoreactivity of monomers by means of photo DSC

The components below were intimately mixed:

5.0 monomer
100 g, camphorquinone
250 mg, p-dimethylaminobenzenesulphonyl-N,N-diallylamide Camphorquinone and p-dimethylaminobenzenesulphonyl-N,N-diallylamide form the photoinitiator system.

The samples were irradiated at 30° C. in a DSC (Differential Scanning Calorimetry) apparatus using a halogen lamp (75 W) with a heat-absorbing filter. The heat flow was recorded as irradiation as a function of the time. Samples of identical composition without a photoinitiator were used as a reference. During the experiment the apparatus was flushed with nitrogen. For the purpose of evaluation, the value t-max was established as the measure of the reaction rate. t-max is the time from the commencement of irradiation to the attainment of the maximum reaction rate (maximal heat flow).

The smaller t-max is, the greater is the photoreactivity.

| Monomer from Table 1 | t-max [min] |
|---|---|
| Monomer 1 | 0.90 |
| Monomer 3 | 0.62 |
| Monomer 6 | 1.06 |
| Monomer 9 | 0.88 |
| Monomer 10 | 0.94 |
| Monomer 11 | 0.72 |
| Comparison: commercial monomer of formula I | 1.85 |
| Comparison: Example 2 of US 4 400 159 | 2.59 |

Example 4
Investigation of the sensitivity to polymerisation inhibition by atmospheric oxygen To determine the layer thickness of the unpolymerised monomer at the free surface (normal ambient atmosphere), cylindrical metal moulds (Ø=5 mm, h=2 mm) were filled with optically activated monomer (activation as in Example 3) and exposed for a period of 20 seconds using a commercial polymerisation unit (Translux® CL, Kulzer GmbH) at a distance of about 2 mm. Immediately after the polymerisation, the height coordinates (z values) were determined in the reflecting microscope by the depth of field method at each of 7 measuring points (x, y) defined by the coordinates of the mechanical stage of the microscope on a straight line, including reference points on the free metal surface. The samples were then washed with ethanol using a medium-hard brush in order to remove the unpolymerised surface layer. The mould was subsequently remounted in the initial position on the mechanical stage of the microscope. The x/y coordinates were set to their initial positions and then the z values were again determined. The value of the difference in height before and after washing with alcohol corresponds to the thickness of monomer which remained at the surface owing to the inhibition of the polymerisation by oxygen.

The thickness of the monomer layer was determined in five samples and are summarised in the Table below as average values and standard deviations:

| Monomer from Table 1 | Layer thickness of the unpolymerised monomer [µm] |
|---|---|
| Monomer 3 | 1.3 ± 0.9 |
| Monomer 6 | 0.9 ± 1.5 |
| Monomer 8 | 2.0 ± 1.5 |
| Monomer 9 | 0.0 ± 1.5 |
| Monomer 10 | 1.0 ± 1.2 |
| Comparison: commercial monomer of formula I | 9.8 ± 2.8 |
| Comparison: Example 2 of US 4 400 159 | 3.2 ± 1.4 |

After having been brushed with ethanol, the comparative samples showed distinct abrasion marks, whereas brush marks were barely discernible on the samples from the monomers of Examples 1 and 2 under the reflecting microscope at 200 times magnification. This observation is evidence of a better surface polymerisation of the samples from the monomers of Examples 1 and 2 in comparison with the reference sample.

We claim:

1. Monomer containing cyclic carbonate groups corresponding to formula III

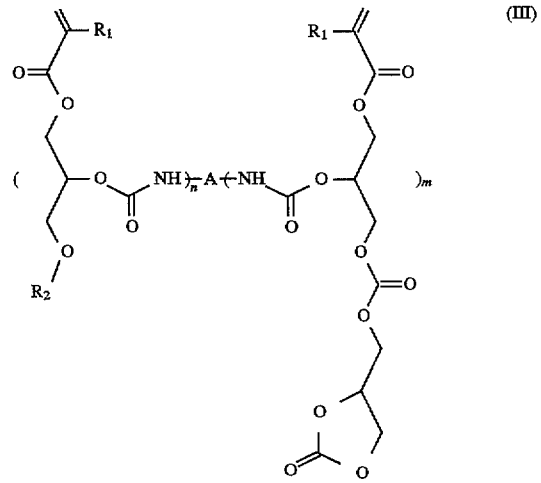

wherein
$R_1$ represents hydrogen or methyl,
$R_2$ represents hydrogen or (meth)acryl,
A represents an n- and m-valent hydrocarbon radical having 2 to 30 carbon atoms, which may be interrupted by one or more ether, ester, anide, urethane or urea groups and may be substituted by one to five (meth) acrylate groups, n signifies an integer from 0 to 3 and m signifies an integer from 1 to 4.

2. Monomer containing cyclic carbonate groups, according to claim 1, corresponding to the formula IIIa

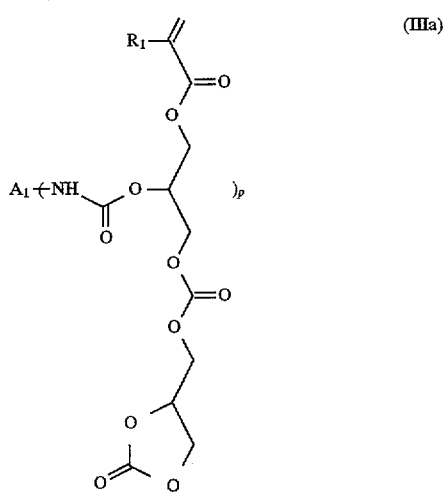

(IIIa)

wherein $R_1$ represents hydrogen or methyl, $A_1$ represents a p-valent hydrocarbon radical having 2 to 30 carbon atoms, which may be interrupted by one or more ether, ester, amide, urethane or urea groups, and p signifies 2 or 3.

3. Monomer according to claim 1, selected from the group comprising

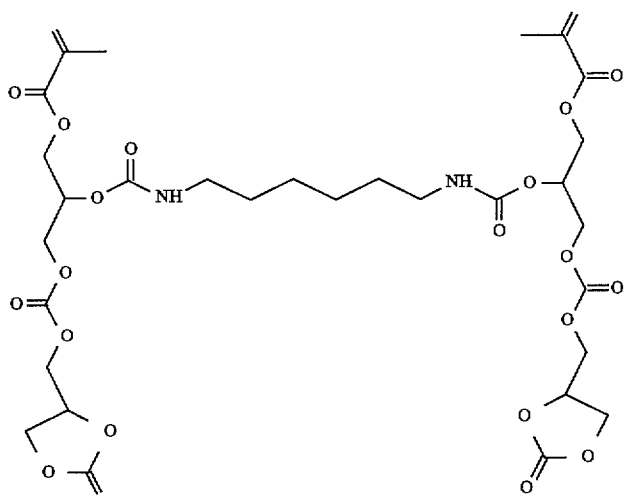

Monomer 1

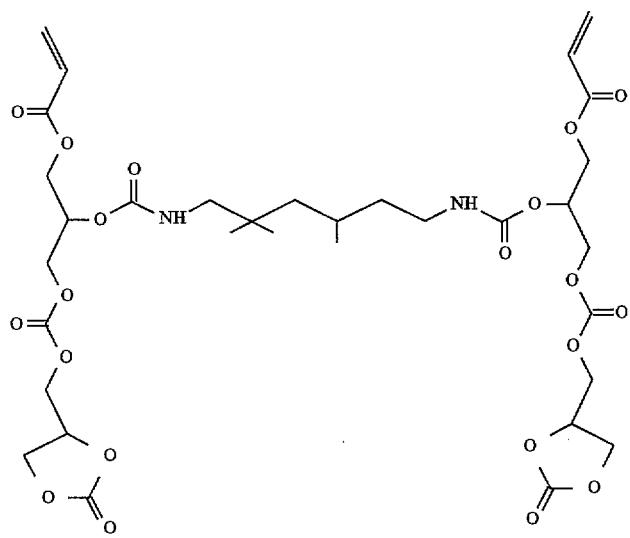
Monomer 2
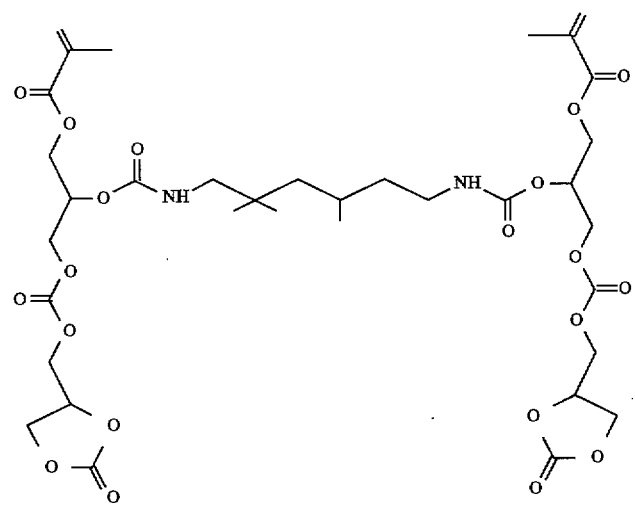
Monomer 3
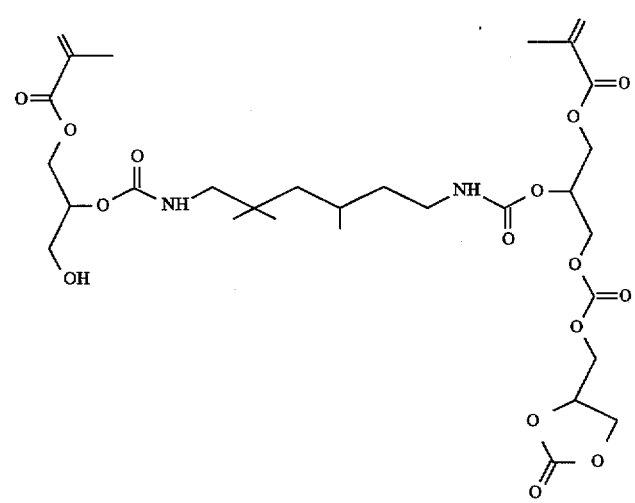
Monomer 4

-continued
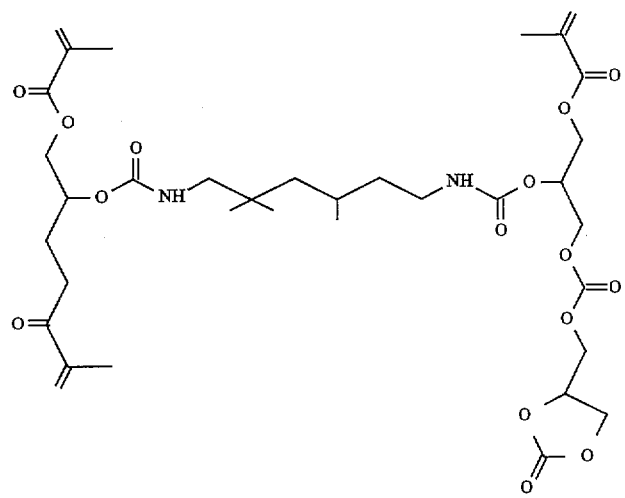
Monomer 5
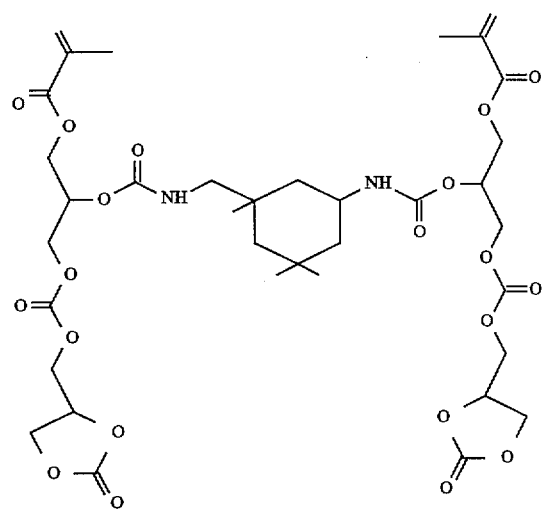
Monomer 6
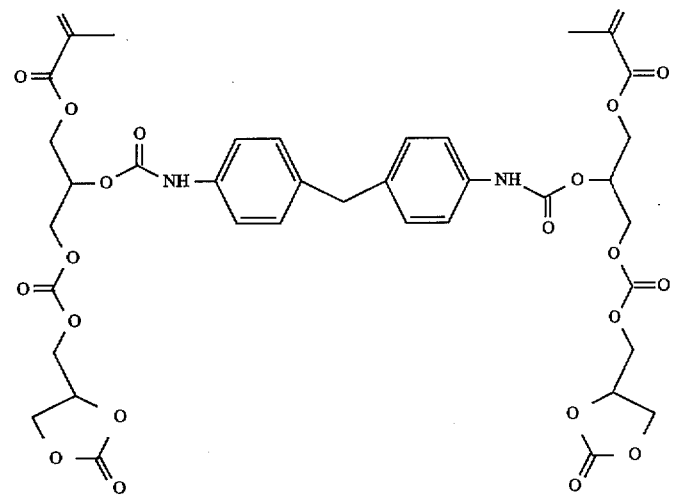
Monomer 7

-continued
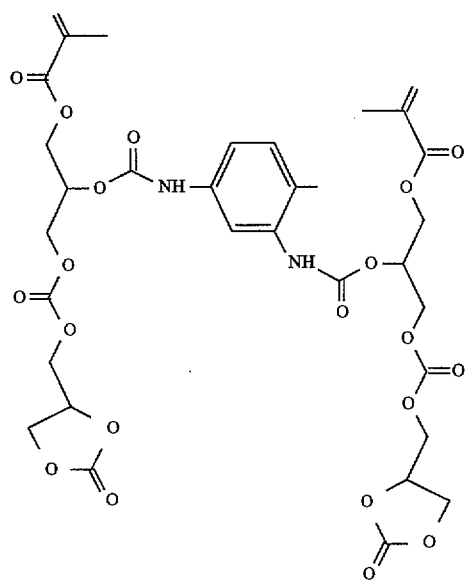
Monomer 8
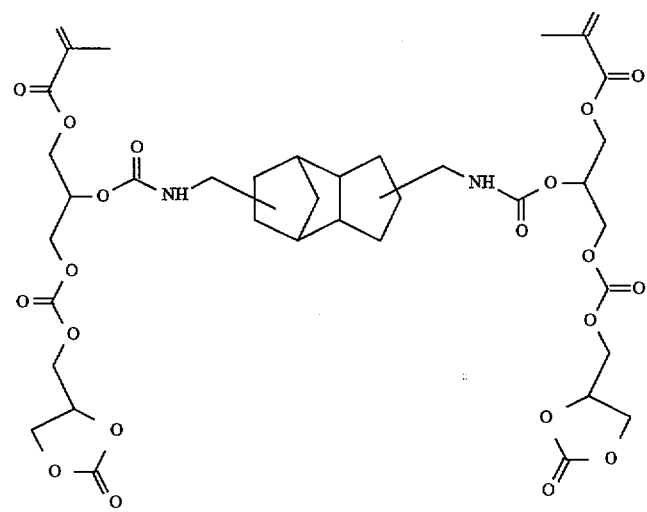
Monomer 9

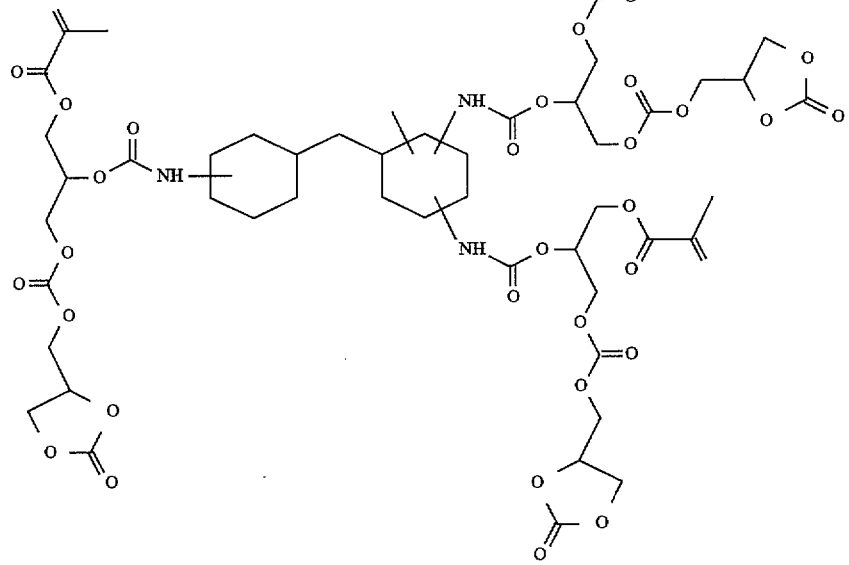
Monomer 10
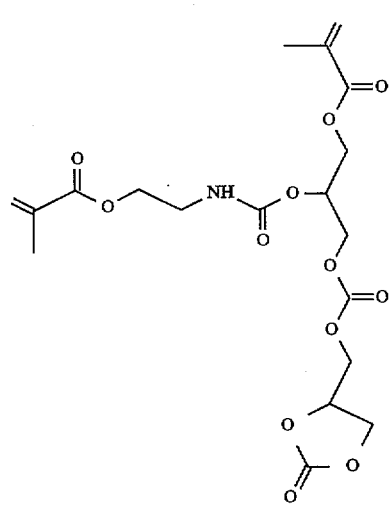
Monomer 11
4. Preparations containing the monomer according to claim 1 and optionally comonomers as well as conventional fillers and auxiliary substances.
* * * * *

UNITED STATES PATENT AND TRADEMARK OFFICE
CERTIFICATE OF CORRECTION

PATENT NUMBER: 5,763,622

DATED: June 9, 1998

INVENTOR(S): Podszun et al.

It is certified that there is an error that appears in the above-identified patent and that said Letters Patent is hereby corrected as shown below:

In column 18, line 65, "anide" should be changed to -- amide--.

Signed and Sealed this

Tenth Day of April, 2001

*Attest:*

NICHOLAS P. GODICI

*Attesting Officer*     *Acting Director of the United States Patent and Trademark Office*